United States Patent
Vieira

(10) Patent No.: US 6,896,196 B2
(45) Date of Patent: May 24, 2005

(54) EVAPORATIVE CONTAINER FOR VOLATILE SUBSTANCES

(75) Inventor: Pedro Queiroz Vieira, Parede (PT)

(73) Assignee: C.T.R. Consultoria Tecnica E Representacoes LDA (PT)

( * ) Notice: Subject to any disclaimer, the term of this patent is extended or adjusted under 35 U.S.C. 154(b) by 343 days.

(21) Appl. No.: 10/050,694

(22) Filed: Jan. 16, 2002

(65) Prior Publication Data

US 2003/0132308 A1 Jul. 17, 2003

(51) Int. Cl.$^7$ ................................................ A24F 25/00
(52) U.S. Cl. ........................... 239/44; 239/42; 239/45; 239/47; 239/50; 239/43
(58) Field of Search .............................. 239/34, 36, 43, 239/44, 45, 50, 57, 47, 53, 55, 42; 222/129, 321, 394, 402.1

(56) References Cited

U.S. PATENT DOCUMENTS

| | | | |
|---|---|---|---|
| 3,028,100 A | * 4/1962 | Xenakis et al. | ............... 239/47 |
| 4,621,768 A | 11/1986 | Lhoste et al. | |
| 4,739,928 A | * 4/1988 | O'Neil | ......................... 239/45 |
| 4,742,960 A | * 5/1988 | Bustillo et al. | ............... 239/47 |
| 5,427,278 A | * 6/1995 | Gardner, III | ................. 222/129 |
| 5,725,152 A | 3/1998 | Akyu | |
| 6,236,807 B1 | * 5/2001 | Ruffolo et al. | ............... 392/390 |

FOREIGN PATENT DOCUMENTS

FR 2804662 8/2001

* cited by examiner

Primary Examiner—Davis Hwu
(74) Attorney, Agent, or Firm—McNair Law Firm, P.A.; Cort Flint

(57) ABSTRACT

A container (1) for volatile substances which can be evaporated by an evaporation device is disclosed having a container body (2) in which the volatile substances are contained. A container neck (3) extends away from the container body (2) in which a container opening (4) is formed. Furthermore, a wick retaining insert (8) in the form of a cylindrical sleeve is provided that can be placed in the container opening (4) of the container neck (3). There is an insert wick passage (9) for the insertion of the wick (10) having an outside wall (13) which presses, at least partially, against an inside container neck wall (15) in a wick clamping connection when inserted. Wick retention is provided by the insert so that wick (10) is secured from being pulled out of the container (1) when inserted. According to the invention wick (10) can be inserted through wick passage (9) of wick retaining insert (8) when the wick retaining insert is not inserted. The wick clamping connection for the wick retention is at least partially made in form of a clamping connection (26) which wedges the wick (10) against an inside wall of wick retaining insert which secures it from being pulled out when the wick retaining insert (8) is inserted.

21 Claims, 3 Drawing Sheets

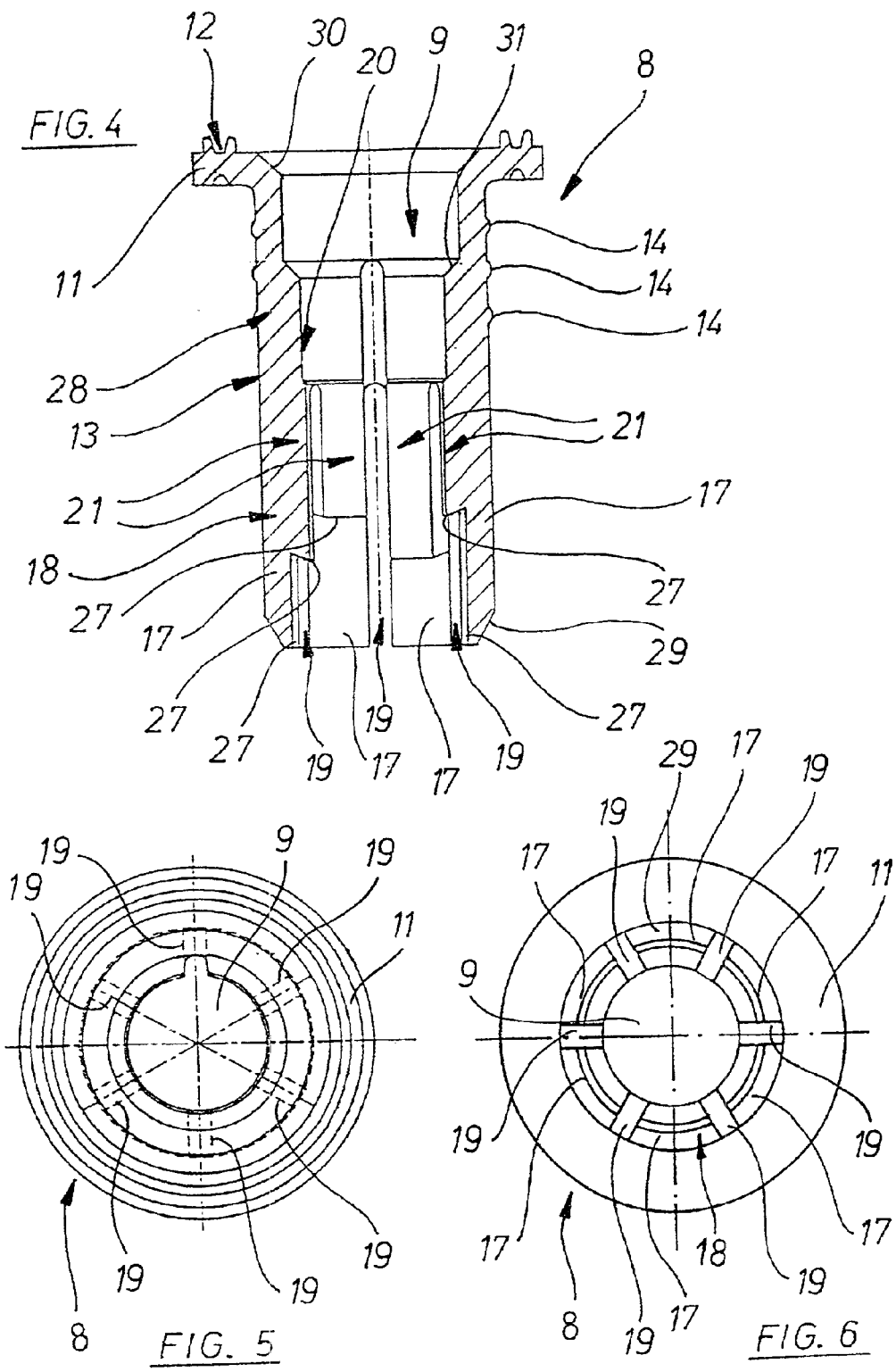

EVAPORATIVE CONTAINER FOR VOLATILE SUBSTANCES

BACKGROUND OF THE INVENTION

This invention relates to a container from which volatile substances such as insecticides and/or aromatics are evaporated by means of an evaporating device.

Containers for substances evaporated by means of an evaporating apparatus are generally known and commonly used such as containers which are screwed or snapped into a housing of the evaporation apparatus. The container comprises a wick with one end dipping into the volatile substance and an opposite end which extends out of the container. The wick end may also extend into a suitable wick opening of a heating element of the evaporation device for heating. The volatile substance is drawn out of the container by the capillary effect so that the substance is evaporated by the heat from the heating element. The heating element may be in the form of a ceramic block. The substance is able to emerge into the environment through ventilation slits in the housing of the evaporation apparatus. The evaporation device is commonly used for the evaporation of volatile substances, such as insecticides and/or aromatics, in closed rooms of apartments or homes.

One problem with prior evaporation systems is that the volatile substances, particularly in the case of pesticides, can in large quantities be dangerous to the health of humans and in particular of children. For example, when the wick is pulled too far out of a full container a greater quantity of the volatile substance becomes accessible which can be spilled. In addition there is a danger, once a container is empty, that a user might fill up the container with a volatile substance that is flammable, and not suitable for use in the evaporation device. A danger may also exist if an empty container is filled with a insecticide that may not be suitable for evaporation in enclosed spaces due to its high toxicity.

In order to prevent these dangers, a container for volatile substances in an evaporation device has been proposed in U.S. Pat. No. 6,236,807. The proposed container includes a container neck extending from the container having a container opening. A wick retaining insert is inserted into the container opening of the neck which is made as a cylindrical insert sleeve. The sleeve is provided with a holding insert and wick opening for the insertion of the wick. An outside wall of the holding ring insert contacts an inside wall of the container neck at least in some areas. This container furthermore comprises a wick-fixing device by means of which the wick is secured when inserted against being pulled out of the container neck. In practice, the wick-fixing device is provided in accordance with the present invention by a needle inserted radially into the container below the wick retaining insert. The inserted needle penetrates through the wick with two opposite needle ends radially extending from the wick. The wick retaining insert is pressed into the container opening of the container neck by means of a press fit so that if an attempt is made to pull the wick out of the container, the needle engages a lower end of the wick retaining insert providing resistance against the pulling out of the wick. The structure must be designed so that the resistance to the pulling out of the wick meets local ordinances, e.g., a United States ordinance recommending a minimum resistance force of 15 lbs.

However, a problem exists with the prior wick-fixing needle in that the needle is inserted initially through a dry wick made up of a fiber material. When the wick is wet by the volatile substance the wick is softened so that the needle may possibly become loose and detached form the wick. The insertion of the wick is no longer ensured. This is a temporary solution that is not sufficient for the requirements of high quality containers.

It is therefore an object of the present invention to provide a container for volatile substances in which a wick is effectively inserted and retained in the container so that accidental removal of the wick is prevented.

SUMMARY OF THE INVENTION

The above objectives are accomplished according to the present invention by providing a container having a wick retaining insert. The wick can be inserted through a wick opening of the wick retaining insert when the wick is not in the container. A clamping connection between the container neck and insert is designed so that the clamping connection causes the wick to be clamped against an inside wall area of the wick retaining insert and prevents it from being puled out when the wick retaining insert is inserted in the opening of the container neck.

The high quality clamping of the wick in the container can be produced easily with good functional reliability. This is achieved in particular by clamping the wick against an inner wall of the wick retaining insert. The clamping connection is formed by existing components so that no separate components have to be provided and the number of components can be reduced. In addition, a flatter clamping of the wick can be achieved for a good and reliable retention.

The retention power of the clamping connection is designed to resist pulling out of the wick. The snap-in force of the wick retaining insert is coordinated to prevent pulling out of the wick together with the wick retaining insert.

The resistance force opposing the pulling out of the wick retaining insert is preferably greater than the clamping power applied by the clamping connection to the wick. In principle, however, the resistance force opposing the pulling out of the wick retaining insert could also be less than the resistance force opposing the pulling out of the wick from the wick retaining insert.

A clamping connection with at least two different diameter zones is preferred so a deformable wick retaining insert clamping zone is provided. The wick retaining insert can be deformed radially along its clamping zone in the direction of the wick as the distance over which the wick retaining insert is inserted increases, so as to clamp the wick securely along the inside wall zone of the wick retaining insert. An actual construction of this type can be realized easily by making the wick retaining insert of a plastic material by extrusion. The deformation of the clamping zone is preferably elastic, i.e., with a return to initial position. In principle, plastic deformation would also be possible, since no re-use of the wick retaining insert is intended or desired. Alternatively, however, other materials or combinations of materials for the wick retaining insert can be used insofar as they are suitable to ensure a deformation of the clamping zone in the described manner.

In an advantageous embodiment, the different diameter zones, at least two, are formed on the inside wall of the container neck. One diameter zone is close to the container opening and another diameter zone is formed in the container neck close to the container body which has a smaller diameter. The clamping zone of the wick retaining insert fits with the different clamping zones on the inside container neck wall so that the insert is deformed radially against the wick to clamp it securely in passing from one diameter zone to the other. Forming the different diameter zones on the inside container neck wall is especially easy and inexpensive to make, especially where glass containers are used. Furthermore, fitting the insert to the inside container neck wall is especially simple when the wick retaining insert is made of an extruded plastic material. In this manner, reliable and advantageous clamping of the wick is ensured preventing it from being pulled out of the container.

While the different diameter zones could, in principle, be conical, this is somewhat more expensive in manufacturing technology. Preferably, the different diameter zones are created by means of radially surrounding steps along the inside container neck so that a greater diameter zone is created above, and a smaller diameter zone below. For easy introduction of the wick retaining insert, an extrance bevel in the direction of the lower, smaller diameter zone can be formed in the area of the steps. This results in an especially high quality construction through which the clamp connection according to the invention can be realized very easily and reliably secure against the wick pulling out.

The wick retaining insert can be provided with a surrounding shoulder at one end that presses against the upper edge of the container opening of the container neck when inserted. This ensures in a simple manner that the wick retaining insert can always be inserted correctly.

In another advantageous aspect of the invention, at least one snap-in element is provided on the outside wall of the wick retaining insert. The snap-in element interacts with a complimentary snap-in element on the inside container neck wall to secure the wick retaining insert in the container neck. This snap-in connection can be established easily by pressing the wick retaining insert into the container opening of the container neck. The snap-in element is preferably formed on the outside wick retaining insert wall in form of at least one circumferential snap ring, and an inside neck wall by a complimentary shaped snap-in groove. With such a design it is possible to achieve a secure connection between the wick retaining insert and the container neck.

In an advantageous embodiment, the wick retaining insert clamping zone includes at least two clamping fingers extending in the direction of a longitudinal wick retaining insert axis. The fingers are radially separated by a gap. The gap between adjacent holding fingers provides sufficient clearance for a radial deformation of the holding fingers in the direction of the wick to clamp the wick. The holding fingers are preferably elastic and return to their original positions.

Especially reliable and secure clamping of the wick is ensured when at least one protrusion-like step is provided on the inside insert wall. This step is pushed into the wick in the manner of a mandrel when the clamping area is deformed in the direction of that wick. The edge of the step is pressed into the wick and the wick is clamped. In a preferred embodiment, the clamping steps of adjoining clamping fingers are offset relative to each in the longitudinal direction of the wick retaining insert. Preferably, every second clamping step is approximately at the same level when a plurality of clamping fingers are used. This offset produces even distribution of the clamping power along the wick. These clamping steps achieve an especially advantageous clamping in the manner of counter-hooks. The clamping steps can in principle be of different designs. However, a design where the gradation decreases from the inside to the outside is preferred.

To be able to insert the wick easily and comfortably through the insert when not inserted into the container opening, at least one radially surrounding entrance bevel is provided in the insert along the longitudinal direction of the insert. Similarly, an entrance bevel can be formed at one end of the wick retaining insert for its insertion into the container opening of the container neck.

In principle the wick retaining insert and its associated container opening may be given a round, angular, or similar cross-section. However, a design in which the wick retaining insert, and the container opening have a circular cross-section is preferred for favorable geometries and simple manufacture of the components.

In another advantageous aspect of the invention, threads are formed on an outside wall of the container neck so that a locking cover can be screwed onto the container neck. Thus, a separate salable unit is produced which can be used, e.g., in different types of evaporation devices. The locking cover provides protection for the wick protruding from the container.

As has been originally explained in connection with the known state of the art, a completely assembled container can be coupled to an evaporation device so that the wick is located with one wick end in the area of a heating arrangement. In an especially preferred manner the container can be screwed into a housing of the evaporation device, preferably by using the threads formed on the outside wall of the container neck for the locking cover. The wick end extends into a wick opening of a heating block of the heating arrangement when the wick end is assembled.

The container body can have geometry, i.e., it can be round, cylindrical, pyramid shaped, etc., with the container being preferably made of a glass material and/or a plastic material.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein:

FIG. 4 is a schematic enlarged cross-section illustrating a wick retaining insert that can be pressed into a container opening of a container neck and is designed in form of a cylindrical sleeve, according to the invention;

FIG. 5 is a schematic enlarged top view illustrating the wick retaining insert of FIG. 4;

FIG. 6 is a schematic enlarged view from below illustrating the wick retaining insert of FIG. 4.

DESCRIPTION OF A PREFERRED EMBODIMENT

Referring now in more detail to the drawings, the invention will now be described in more detail.

Figure 1:
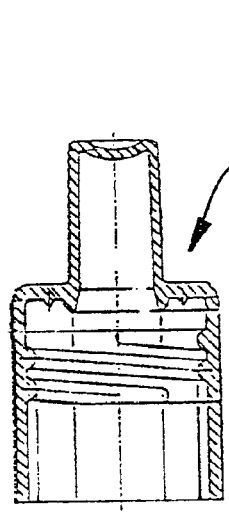
FIG. 1 is a schematic cross-section view illustrating a locking cover for a container, according to the invention.

FIG. 1 schematically shows a side view of a container 1 for substances to be evaporated by means of an evaporation device (not shown) such as insecticides and/or aromatics. FIG. 3 shows a schematic top view of container 1 of FIG. 2. Container 1 is preferably made of a glass material.

Figure 2:
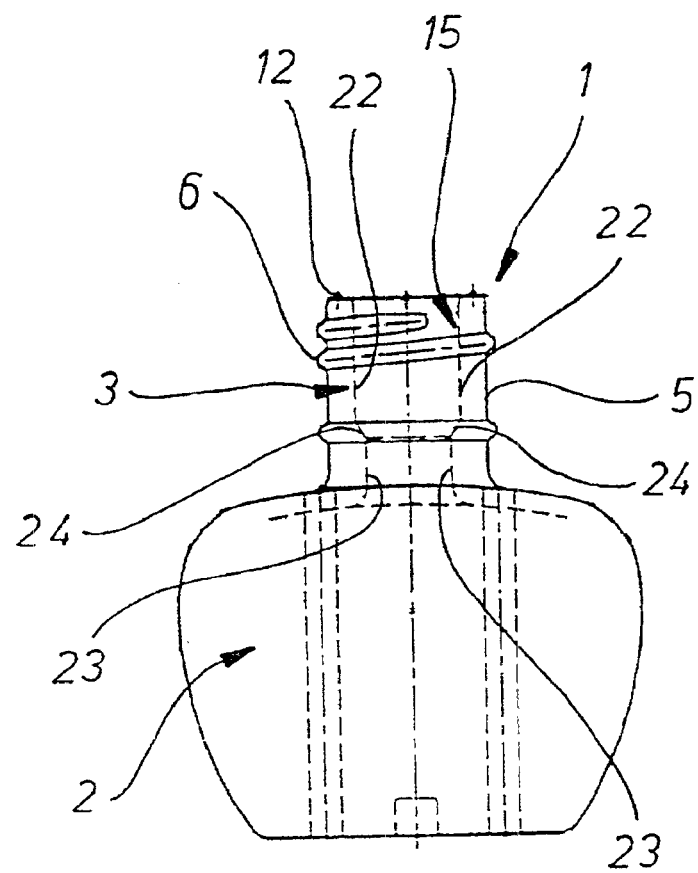
FIG. 2 is a schematic side view of a container, according to the invention.
Figure 3:
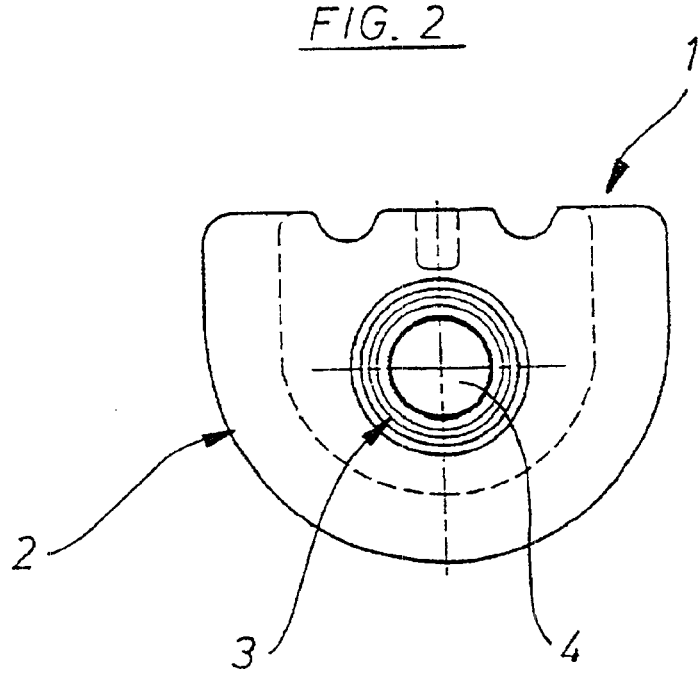
FIG. 3 is a schematic top view of the container of FIG. 2, according to the invention.

As can be seen in FIGS. 2 and 3, container 1 has a container body 2 which can contain a volatile substance. A container neck 3 extends from container body 2 and a container opening 4 is formed in the neck. The form of the container body 2 is chosen here merely as an example. In principle, the container body 2 can be designed with any desired and required geometries.

Figure 7:
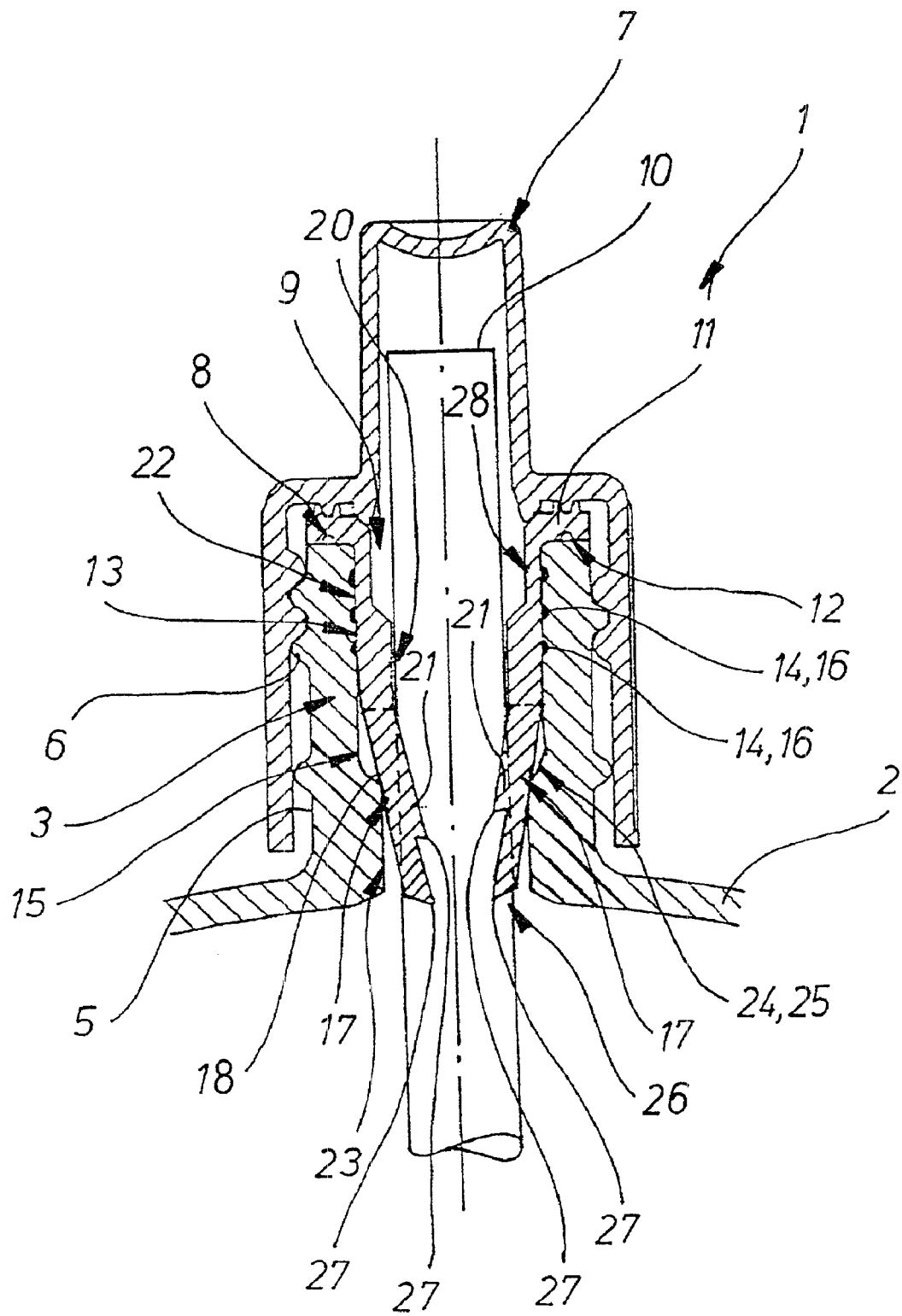
FIG. 7 is a schematic enlarged cross-sectional view illustrating a partial section of a completely assembled container in which a clamping connection holds the wick inserted through the wick retaining insert clampingly against an inside wick retaining insert zone and secures it against being pulled out, according to the invention.

As can be seen, especially in FIG. 2, the container neck 3 has an outside wall 5 with threads 6, so that a locking cover 7, shown schematically in FIGS. 1 and 7, can be screwed on container neck 3 in the assembled state of container body 2.

FIG. 4 shows an enlarged, schematic cross-sectional view of a wick retaining insert 8 that can be pressed into the container opening 4 of the container neck 3 and is made in the form of a cylindrical sleeve. This wick retaining insert 8 is completely traversed by a wick passage 9 through which a wick 10 (FIG. 7) can be inserted. FIG. 5 shows a corresponding enlarged schematic top view of wick retaining insert 8, while FIG. 6 shows a schematic view from below.

As can be seen in FIGS. 4 through 6, wick retaining insert 8 is provided at one end with a surrounding insert shoulder 11 which lies on an edge 12 of container opening 4, as can be seen in FIG. 7. As can further be seen in FIGS. 4 and 7, there are three radially circumferential snap-in rings 14 spaced from each other in a longitudinal direction. The snap-in rings mesh with or snap into complimentary snap-in grooves 16 formed in the interior of container neck 6 when wick retaining insert 8 is inserted, as shown in FIG. 7. In that case wick retaining insert 8 is preferably pressed into the container opening 4 of the container neck 3 with a press fit at least in some areas. A contact connection is provided by the snap-in connection constituted by snap-in rings 14 and snap-in groove 16 which provides additional safety against pulling out the wick retaining insert 8 from the container opening 4.

As can be seen in FIG. 4, in combination with FIG. 7, wick retaining insert 8 is provided with a clamping zone 18 for clamping the wick in the insert which includes, in this example, five clamping fingers 17. These clamping fingers 17 extend in the direction of the longitudinal axis of the wick retaining insert and are separated from each other circumferentially by gaps 19.

As can be seen in particular in FIGS. 4, 6, and 7, clamping steps 21 are formed on clamping fingers 17 on an inside insert wall 20. The clamping steps 21 of the clamping fingers 17 adjoining each other are offset relative to each other in the longitudinal direction of the wick retaining insert. Every other clamping step 21 is approximately at the same level as related to the longitudinal axis of the wick retaining insert. With this kind of design of the clamping steps 21 their gradation is downward from inside to outside.

As can best be seen in FIGS. 2 and 7, the illustrated container neck 3 has two different diameter zones 22, 23 formed by simple gradation 24 in a change-over zone between diameter zones 22, 23. Diameter zone 22 constitutes an upper, greater diameter zone, and diameter zone 23 constitutes a lower, smaller diameter zone. As can be seen in particular in FIG. 7, an insertion bevel 25 is provided in the area of the gradation 24.

A clamping connection 26 is created between wick retaining insert 8 and inside container neck wall 15, caused by the different diameter zones 22, 23 at clamping zone 18 of the insert. This clamping connection is formed by deformation of the clamping fingers 17 against inside container neck wall 15 according to the invention to clamp and fix the inserted wick 10 so that the wick is secured against being pulled out of the container 1, as explained in further detail below.

Before wick retaining insert 8 is inserted into container opening 4 of container neck 3, it is in the condition shown in FIG. 4. In this condition, wick 10 can simply be inserted through holding ring wick opening 9 of the insert. When the wick is inserted in wick retaining insert 8 the assembly is pressed into container opening 4 and container neck 3, whereby the clamping fingers 17 of the wick retaining insert 8 pass through the upper diameter zone 22 through the insertion bevel 25 into the smaller diameter zone 23, so that they care deformed in the direction of the wick 10 as can be seen in particular in FIG. 7. As a result, the step edges of clamping fingers 17 are pressed against the wick 10 so that the wick 10 is prevented by a certain resistance force from being pulled out. The deformation of the clamping fingers 17 at clamping zone 18 is effected by gaps 19 providing sufficient room for the deformation of the clamping fingers 17 in the direction of the wick 10.

Clamping connection 26 is designed in form of a clamping cone connection, whereby wick retaining insert 8 is preferably made of a plastic material and the clamping fingers are preferably elastically deformable. However a plastic deformation is also a possible alternative.

As can further be seen in FIG. 7, there is an upper wick retaining insert zone 28 that starts above the broken line FIG. 7 and is pressed into container opening 4 by means of a press fit. To facilitate the insertion of wick retaining insert 8 at the beginning of the snap-fitting process, an insertion bevel 29 is formed across from the shoulder 11. To facilitate the insertion of the wick 10 into the wick retaining insert 8, insertion bevels 30, 31 are also provided.

While a preferred embodiment of the invention has been described using specific terms, such description is for illustrative purposes only, and it is to be understood that changes and variations may be made without departing from the spirit or scope of the following claims.

What is claimed is:

1. A container for volatile substances, such as insectices and aromatics which are evaporated by an evaporation device, the evaporation device having a container body for containing the volatile substance, a container neck extending from the container body terminating in a container opening in which a wick may be inserted, a wick retaining insert inserted into the container opening of the container neck for holding the wick in the container, said wick retaining insert having an outside insert wall at least partially in contact connection with an inside container neck wall when inserted, and a wick fixing device which secures the wick against being pulled out of the container when inserted, wherein said container comprises:

a wick retaining insert;
a wick opening formed in an upper portion of said wick retaining insert;
a container opening formed in said container neck;
a contact connection for fixing said wick retaining insert in the container opening;
a clamping connection for clamping a wick within said wick retaining insert when said wick retaining insert is fixed in said container opening by said contact connection so that said clamping connection of said wick retaining insert secures the wick against being pulled out; and said container neck includes at least two diameter zones having different diameters, and said wick retaining insert includes a deformable clamping zone between said container neck and said wick retaining insert atone of said diameter zones; and said wick retaining insert being radially and inwardly deformable at said clamping zone when inserted in said container neck to clamp the wick against an inner wall area of the wick retaining insert.

2. The device of claim 1 wherein said two different diameter zones are formed on an inside container neck wall so that a first diameter zone closest to the container opening has a greater diameter than a second diameter zone closest to the container body so that said wick retaining insert engages said diameter zones on the inside container neck wall in such manner that said wick retaining insert is deformed in said radial direction to clamp the wick during insertion when going from said first diameter zone to said second diameter zone.

3. The device of claim 2 wherein said first and second diameter zones are formed by a radially circumferential gradation in an area of the inside container neck so that said first diameter zone is formed as an upper diameter zone and said second diameter zone is formed as a lower diameter zone.

4. The device of claim 3 including an insertion bevel formed on said wick retaining insert in the direction of said second, lower diameter zone in the area of said gradation.

5. The device of claim 1 wherein said wick retaining insert has a circumferential insert shoulder at one end which engages an edge of said container opening when the wick retaining insert is inserted.

6. The device of claim 1 including at least one snap-in element provided on an outside wall of said wick retaining insert, said snap-in element interacting with a complimentary element formed on an inside wall of said container neck to provide a snap-in connection between said insert and container neck that can be unsnapped.

7. The device of claim 1 wherein said clamping connection includes a clamping zone on the wick retaining insert formed by at least two clamping fingers extending in the direction of the longitudinal axis of the insert and a gap being defined between said clamping fingers allowing said fingers to deform and clamp said wick.

8. The device of claim 7 wherein said clamping fingers and said wick retaining insert clamping zone are elastically deformable.

9. The device of claim 8 including at least one clamping step formed on said clamping fingers on an inside wall of said insert having an edge which is pushed into the wick when the wick is clamped.

10. The device of claim 9 wherein said clamping steps of adjoining clamping fingers are offset relative to each other in the longitudinal direction of the wick retaining insert whereby every other clamping step is preferably located at the same level when three clamping fingers are used.

11. The device of claim 1 wherein a clamping step is formed on an inside wall of said wick retaining insert near the clamping zone which can be pressed into the wick for clamping the wick when the insert is deformed.

12. The device of claim 1 including a circumferential insertion bevel provided in said insert wick opening for easy insertion of the wick.

13. The device of claim 12 including an insertion bevel formed on an entry end of said wick retaining insert to aid in inserting the retaining insert into said container opening of the container neck.

14. The device of claim 13 that the wick retaining insert and said container opening have an approximately circular cross-section in the container neck.

15. The device of claim 1 including threads formed on one outside wall of said container neck and a locking cover screwed on the container neck to form a complete individual assembly.

16. The device of claim 1 wherein the container neck includes threads on an outside area so that said container may be screwed into a housing of an evaporation device with the wick end extending into a wick opening of a heating block of the heating device when assembled.

17. The device of claim 1 wherein the resistance force of the wick retaining insert against being pulled out from the container neck is greater than the resistance force of the wick against being pulled out of wick retaining insert.

18. A container for volatile substances, such as insecticides and aromatics which are evaporated by an evaporation device comprising:

a container body for containing the volatile substance;

a container neck extending from the container body terminating in a container opening;

a unitary wick retaining insert for insertion into said container opening having a wick passage formed by an inside wall of said wick retaining insert for receiving the wick;

said wick retaining insert having an outside wall at least partially in contact with an inside wall of said container neck when placed in said neck;

a contact connection between said container neck and wick retaining insert for fixing said insert in the container neck;

a wick clamping connection between said inside wall of said retaining insert and the wick for clamping the wick in said wick retaining insert when said insert and wick are placed in said container neck; and said wick clamping connection includes a plurality of resilient clamping fingers forming at least part of said wick passage, and at least one abutment carried in said container neck engaging said clamping fingers to bend said clamping fingers inwardly to clamp against the wick when said wick retaining insert is placed in said container neck.

19. The device of claim 18 wherein said container neck includes diameter zones having different diameters, and said inside wall of said wick retaining insert is deformable to provide a wick clamping zone so that inside wall of said retaining insert is deformed to clamp the wick against said inside wall of said insert wick passage at one of said diameter zones as the insertion distance of the wick retaining insert increases through said diameter zones.

20. The device of claim 18 including clamping steps formed on said clamping fingers which are offset in the longitudinal direction of said wick passage.

21. A container for volatile substances, such as insecticides and aromatics which are evaporated by an evaporation device comprising:

a container body for containing the volatile substance;

a container neck extending from the container body terminating in a container opening;

a unitary wick retaining insert for insertion into said container opening having a wick passage formed by an inside wall of said wick retaining insert for receiving the wick;

said wick retaining insert having an outside wall at least partially in contact with an inside wall of said container neck when placed in said neck;

a contact connection between said container neck and wick retaining insert for fixing said insert in the container neck;

a wick clamping connection between said inside wall of said retaining insert and the wick for clamping the wick in said wick retaining insert when said insert and wick are placed in said container neck; and said container neck includes diameter zones having different diameters, and said inside wall of said wick retaining insert is deformable to provide a wick clamping zone so that inside wall of said retaining insert is deformed to clamp the wick against said inside wall of said insert wick passage at one of said diameter zones as the insertion distance of the wick retaining insert increases through said diameter zones.

* * * * *